United States Patent [19]

Kusakabe et al.

[11] Patent Number: 5,552,287
[45] Date of Patent: Sep. 3, 1996

[54] MONOCLONAL ANTIBODY SPECIFIC FOR ANTIGENS IN MOUSE INBRED STRAINS

[75] Inventors: Moriaki Kusakabe, Wako; Teruyo Sakakura, Tsu, both of Japan

[73] Assignee: Rikagaku Kenkyusho, Wako, Japan

[21] Appl. No.: 261,301

[22] Filed: Jun. 16, 1994

Related U.S. Application Data

[63] Continuation of Ser. No. 944,650, Sep. 14, 1992, abandoned.

[30] Foreign Application Priority Data

Dec. 26, 1991 [JP] Japan ...................... 3-344608

[51] Int. Cl.$^6$ .................................. G01N 33/573
[52] U.S. Cl. ..................... 435/7.4; 435/960; 436/519; 530/388.2; 530/388.85
[58] Field of Search .................... 435/7.21, 7.4, 435/960; 436/519, 548; 530/388.2, 388.85

[56] References Cited

PUBLICATIONS

Kusakabe, et al. J. Cell Biol., 107, 257–265 (1988).
Kusakabe et al., 1988, A novel methodology for analysis of all distribution in chimetic mouse organs using a strain specific antibody. J Cell Biol. 107: 257–265.
Lee et al., Jun. 1991, Strain specific sensitivity to diethylmitrosamine–induced carcinogenesis is maintained in chepatocytes of C3H/HeN←→C57BL/6N chimeric mice, Cancer Res 51: 3257–3260.
Goding, 1983. Monoclonal Antibodies: Principles and Practice.
Production and Application of Monoclonal Antibodies in Cell Biology, Biochemistry and Immunology. Academic Press, Orlando, pp. 8, 40, 56–97.
Mosmann et al., 1989. TH1 and TH2 cells: different patterns of lymphokine secretion lead to different functional properties. Ann. Rev Immunol. 7: 145–173.

Primary Examiner—James C. Housel
Assistant Examiner—Gary Tanigawa
Attorney, Agent, or Firm—Oblon, Spivak, McClelland, Maier, & Neustadt, P.C.

[57] ABSTRACT

A novel monoclonal antibody of IgG1/κ subclass, characterized in that it recognizes antigens specifically present in mouse inbred strains consisting of DBA/1, CE/J, SM/J, IQI, PL/J, SWM/Ms, RIIIS/J, RFM/MsNrs and C3H and its congenic mouse strains thereof, wherein one of said antigens has a molecular weight of 66,000 and the other has a molecular weight of 68,000 and said antigens are present in the mitochondria of C3H mouse strain.

The present invention also provides a hybridoma cell line which produces the above monoclonal antibody, a method for identifying the origin of a cell derived from a mouse, and a reagent for identifying the origin of a cell derived from a mouse.

4 Claims, No Drawings

MONOCLONAL ANTIBODY SPECIFIC FOR ANTIGENS IN MOUSE INBRED STRAINS

This is a continuation of application 07/944,650 filed Sep. 14, 1992, now abandoned.

BACKGROUND OF THE INVENTION

The present invention relates to hybridoma cell lines and monoclonal antibodies produced thereby. More specifically, the present invention relates to novel hybridoma cell lines which produce a monoclonal antibody specific for antigens present in cells derived from specific mouse inbred strains and to the monoclonal antibodies produced thereby.

The genetic background of mouse inbred strains is characterized by a wide variety of gene markers. These markers are effective tools for classifying mouse strains. Recent years have seen rapid development of genetic engineering and embryological engineering technologies. One example is the chimeric mouse reported by Tarkowski in 1961 (Nature, 190: 857–860). This mouse is constituted with at least two cell populations derived from different origins and has been used as an experimental strain for investigating environmental factors affecting developmental mechanisms, cancer developmental mechanisms and gene expression. As tissue analysis is required for the analysis of chimeric mice, numerous methods for identifying the origins of cells which constitute the chimeric tissues have been developed. Analysis of a chimeric mouse by an immunohistochemical method using antibodies has been reported (H-2; Ponder, B. A. J., et al., J. Embryol. Exp. Morpho., 76: 83–93, 1983 and GPI; Oster-Granite, M. L. & Gearhart, Dev. Biol., 85:199–208, 1981). However, the method is not effective because it can not sufficiently analyze the chimerism of all tissues in an individual.

One of the inventors reported an effective method for analyzing the chimerism of all tissues in an individual using polyclonal antibodies(J. Cell Biol., 107, 257–265, 1988). However, in this method, only an extremely small number of antibody-producing animals were obtained by immunizing between mouse strains and the antiserum of each antibody-producing animal had different specificity for an antigen specific to the mouse strain. The most significant disadvantage of the method was that only a small amount of the antiserum was obtained.

SUMMARY OF THE INVENTION

Accordingly, an object of the present invention is to provide a hybridoma cell line which produces a monoclonal antibody specific for antigens present in specific mouse strains and the monoclonal antibody produced thereby.

Another object of the present invention is to provide a method of preparing the monoclonal antibody.

Another object of the present invention is to provide a method for identifying the origin of a cell derived from a mouse, which comprises reacting said cell with the monoclonal antibody.

A further object of the present invention is to provide a reagent for identifying the origin of a cell derived from a mouse.

The present invention provides a monoclonal antibody of IgG1/κ subclass, characterized in that it recognizes antigens specifically present in mouse inbred strains consisting of DBA/1, CE/J, SM/J, IQI, PL/J, SWM/Ms, RIIIS/J, RFM/MsNrs and C3H strains and congenic mouse strains thereof, wherein one of said antigens has a molecular weight of 66,000 and the other has a molecular weight of 68,000 and said antigens are present in the mitochondria of C3H mouse strain.

Further, the present invention provides hybridoma cell lines which produce the above monoclonal antibody.

In addition, the present invention provides a method of preparing the monoclonal antibody, which comprises culturing the hybridoma cell line in a suitable medium and recovering said monoclonal antibody from the culture supernatant of said hybridoma cell line.

The present invention also provides a method of preparing the above monoclonal antibody, which comprises injecting into an appropriate animal the above hybridoma cell line and recovering said antibody from the malignant ascites or serum of said animal.

In addition, the present invention provides a method for identifying the origin of a cell derived from a mouse, which comprises reacting said cell with the monoclonal antibody.

The monoclonal antibody of the present invention can be used as a reagent for identifying the origin of a cell derived from a mouse, if desired, in combination of other reagents. Thus, the present invention provides a reagent for identifying the origin of a cell derived from a mouse, which comprises a monoclonal antibody of IgG1/κ subclass characterized in that it recognizes antigens specifically present in mouse inbred strains consisting of DBA/1, CE/J, SM/J, IQI, PL/J, SWM/Ms, RIIIS/J, RFM/MsNrs and C3H and its congenic mouse strains thereof, wherein one of said antigens has a molecular weight of 66,000 and the other has a molecular weight of 68,000 and said antigens are present in the mitochondria of C3H mouse strain.

DETAILED EXPLANATION OF THE INVENTION

The present invention will be hereinafter explained in more detail.

(Antigen Preparation)

The immunizing antigen preparation can be produced as follows: Organs of a C3H mouse strain such as liver, muscle, kidney, brain, small intestine, large intestine, ventriculus, lung, testis, ovary and uterus are homogenized in a buffer such as Tris-HCl buffer and the homogenate is centrifuged to collect a supernatant. Ammonium sulfate is added to the supernatant and the resulting mixtures are centrifuged to collect a precipitate. After the precipitate is dissolved in a buffer such as Tris-HCl buffer, insoluble components are removed by centrifugation and a supernatant is collected. The supernatant is fractionated by molecular sieve column chromatography. After glucose phosphate isomerase activity is detected in each fraction and the active fractions are combined, the combined active fraction is dialyzed against PBS, phosphate buffered saline, or the like to prepare an antigen solution.

(Immunization)

A variety of mouse strains, rats, rabbits, sheep, horses, cattle and the like are immunized with the antigen solution obtained above.

Alternatively, the antigen solution can be used as mixed with an adjuvant. Examples of the adjuvants include Freund's complete adjuvant containing *Mycobacterium tuberculosis,* Freund's complete adjuvant free from bacteria, alum, killed *Bordetella pertusis, Escherichia coli* lipopolysaccharide, fine particles of nitrocellulose and cellulose acetate. When an adjuvant is used, the antigen solution and an equal volume of the adjuvant can be suspended in PBS, physiological saline, or the like to prepare 0.1–1 mg/ml of an antigen suspension.

Animals are immunized with the antigen suspension. For example, a mouse can be effectively immunized by a priming immunization by intralymphonodical, intradermical, intrasplenical, intraperitoneal, or intravascular injection of 300 μl of the suspension comprising the antigen solution and Freund's complete adjuvant and a subsequent booster immunization by injecting 100 μl of the same suspension from three to five times at intervals of 1–2 weeks.

The blood of the immunized animal is sampled and coagulated at room temperature. Then the resulting blood is centrifuged at 3000 rpm to collect a serum. The primary cultured cells which are prepared with embryos derived from BALB/c and C3H strains are fixed with 95% ethanol containing 1% acetic acid and the fixed samples are immunohistochemically stained using the obtained serum to detect the antibody production of the immunized animal.

(Antibody-Producing Cell Preparation)

Antibody-producing cells can be obtained by isolating antibody-producing cells from lymph node cells, spleen cells, thymocyte cells, peripheral blood cells, or the like. For example, when spleen antibody-producing cells are selected, the spleen is removed and then washed with Eagle's minimum basal medium (hereinafter referred to as "MEM") or RPMI1640 medium (available from GIBCO) several times to obtain antibody-producing cells.

(Myeloma Cell Preparation)

A wide variety of animal cell lines derived from mice, rats, rabbits, humans and the like can be used as myeloma cells for cell fusion. The cell line to be used is preferably drug-resistant and, therefore, is able to grow in a selective medium after cell fusion but not before cell fusion. The most popular cell line is an 8-azaguanine-resistant one, which is not able to grow in a hypoxanthine aminopterin thymidine medium (hereinafter referred to as "HAT medium") because it is defective in hypoxanthine phosphoribosyl transferase. In addition, the cell line is preferably a non-secretor one i.e., a myeloma cell which synthesizes the light chains of immunoglobulins and does not secrete them outside the cell. Examples of such cell lines include P3-X63-Ag8U1(P3U1), P3-X63-Ag8·6·5·3(X63.6·5·3), P3 -NS1-1-Ag4-1(NS-1), and Sp2/0-Ag14(SP2) derived from mouse myeloma MOPC- 21 cell line, rat myeloma 210·RCY3Ag1·2·3(Y3·Ag1.2.3), human myeloma U-266-AR1, and GM15006TG-A12.

(Cell Hybridization)

For the cell fusion, the antibody-producing cells derived from the immunized animal can be fused with $1\times10^7$–$1\times10^8$ myeloma cells in a ratio by cell number ranging from 1:4 to 1:10 at 37° C. for 2–3 minutes in a culture medium for animal cells such as MEM or RPMI1640 using a cell fusion accelerator such as polyethylene glycol (PEG) having an average molecular weight of 1,000–6,000, polyvinyl alcohol, viruses, and the like. PEG having an average molecular weight of 4,000 is preferable.

(Screening of Hybridoma)

Hybridomas may be screened from the cell mixtures after the cell fusion by selectively growing the cell mixtures in a selective medium. For example, the cell mixtures are suitably diluted with RPMI1640 medium containing 15% bovine fetal serum and the diluted cell mixtures are dispersed on a microtiter plate at a density of $5\times10^4$–$1\times10^5$ cells/well. Then a selective medium such as HAT medium is added to each well and the cell mixtures are incubated while replacing the culture medium with a fresh selective medium at suitable intervals. If 8 -azaguanidine-resistant cells are selected as the myeloma cells and HAT medium is used as the selective medium, the unfused myeloma cells die in 10 days after the incubation and those antibody-producing cells which are normal cells are also not able to grow for a prolonged period in vitro. Therefore, cells which grow 10–14 days after the incubation are believed to be hybridomas.

(Screening of Hydridoma)

Anti-mouse antibodies specific to mouse strains in the culture supernatant of the hybridoma may be screened using cultured embryo cells derived from each mouse strain and the specificity of the antibody can be tested by Western blotting. In preferred embodiments, 9–10 day embryos derived from each mouse strain (C3H and BALB/c) are washed with a buffer such as phosphate buffered saline (PBS), Hank's balanced salt solution (HBSS), or the like and then chopped with a scalpel or razor. The chopped tissues are digested with a Trypsin solution to obtain separated cells. The enzyme activities of trypsin cells are inactivated by adding a medium containing fetal calf serum and then the cells are incubated on sterilized slide glass or cover glass for 24–48 hours. The incubated cells attached to the glass are fixed by being immersed in 95% ethanol containing 1% acetic acid for 1–1.5 hours, dehydrated with absolute ethanol, dried and then preserved in a freezer at a temperature ranging from −20° to −80° C. When the fixed cells are used, they are immersed in PBS to return them to the wet condition and then reacted with PBS containing 5% normal goat serum and 1% bovine serum albumin (BSA) for 20–30 minutes to block non-specific adsorption. The blocking solution is blotted by filter paper and then the culture supernatant of hybridomas is reacted with cells derived from each mouse strain for 1–1.5 hours. After the resulting supernatant is washed with PBS, Tris-HCl saline (TBS), or the like, antigen-antibody complexes are detected using fluorescent anti-mouse antibodies. Fluorescent granules are detected in the cytoplasm of a cell to which a culture supernatant containing antibodies having binding strength to the antigens is added (positive reactivity). A hybridoma supernatant is selected if it is reactive with the cells derived from C3H strain but not reactive with the cells derived from BALB/c mouse strain.

The specificity of the anti-mouse strain specific antibody in the culture supernatant of the hybridoma is examined by Western blotting as follows:

An organ such as liver, kidney, or the like derived from C3H mouse strain is removed. A buffer such as PBS, TBS or the like is added to the organ in an amount of 10 ml per 1 g of the organ and subsequently the organ is homogenized by ultrasonic apparatus. The homogenate is cetrifuged at 40,000 rpm and soluble components in the supernatant are collected. After the proteins contained in the thus-obtained solution are denaturated by heating in the presence of β -mercaptoethanol, the protein components are separated by SDS-polyacrylamide gel electrophoresis using a conventional method. The electrophoresis can be carried out using 10% homogenous polyacylamide gel or 4–15% polyacrylamide gradient gel. After the electrophoresis, the gel is brought into close contact with a nitrocellulose or nylon membrane and then the proteins separated in the gel are transferred from the gel to the membrane in Tris-glycine solution (0.025M–0.195M) containing 10–20 % of methanol but not containing SDS, at 4° C. for 10 hours at a voltage of 50–75V. The membrane blotting the proteins is immersed into TBS (blocking solution) containing 5% normal goat serum and 1% BSA to block non-specific adsorption portions of the proteins. Subsequently, the proteins are reacted at room temperature for 16 hours with the supernatant of the hybridomas which showed positive reactivity by the immunohistochemical method. After being washed with cold TBS for 15 minutes three times, the mixtures are reacted with goat anti-mouse IgG antibodies diluted with the blocking solution to a concentration of 10 μg/ml for 3 hours at room temperature and then washed in the same way as shown above. The reaction mixtures are reacted with a mouse PAP solution diluted with the blocking solution to a concentration of 40 μ g/ml for 2 hours and fully washed with cold TBS. Supernatants of hybridomas producing antibodies which react with a protein having a molecular weight of 66,000 and a protein having a molecular weight of 68,000 are selected by detecting positive proteins with a color producing reagent.

(Cloning of Hybridoma)

Since two or more kinds of hybridomas may be growing in each well, cloning of hybridomas can be carried out by means of limiting dilution or the like to obtain hybridomas producing monoclonal antibodies.

(Antibody Production)

A monoclonal antibody can be obtained by a method which comprises culturing the hybridoma in a suitable culture medium for animal cells such as RPMI1640 containing 10–15% fetal calf serum or serum-free medium and recovering the monoclonal antibody from the culture supernatant of said hybridoma. Conventional methods for culturing animal cells and conditions therefor may be modified to apply in the present invention. An alternative way of obtaining a high concentration of a monoclonal antibody is to grow the hybridoma within the abdominal cavity of an animal derived from the same strain as that of the parent myeloma cells or an untreated nude mouse, to which pristane (2,6,10, 14-tetramethyl pentadecane) is injected i.p. The hydridoma forms ascites tumor in 10–18 days after the injection and a high concentration of a monoclonal antibody (about 1–20 mg/ml) stimultaneously appears in the serum and the ascites. If desired, after precipitation with ammonium sulfate, the monoclonal antibody can be purified by DEAE cellulose ion exchange chromatography, affinity column chromatography, or the like.

Examples of thus-obtained hydridoma cell lines include 17-6 strain and 18-15 strain. These hybridoma cell lines produce monoclonal antibodies which recognize the cells derived from C3H mouse strain.

The cell lines designated 17-6 and 18-15 were deposited with the Fermentation Research Institute (1-3, Higashi 1 chome Tsukuba-shi Ibaraki-ken 305, JAPAN) on Dec. 16, 1991 as FERM 12640 and 12641 respectively, which were renumbered FERM BP-3763 and BP-3764 respectively, on Feb. 24, 1992, under the terms of the Budapest Treaty. All restrictions on the availability to the public of the deposited cells will irrevocably removed upon the granting of patent on the present application.

The monoclonal antibody of the present invention is useful for identifying the origin of a cell derived from a mouse.

The monoclonal antibody of the present invention is useful for effectively analyzing the chimerism of all the tissues in a mouse individual.

In addition, identification of the origin of a cell using the monoclonal antibody of the present invention reveals the mechanism of development and differentiation, cancer development, and gene expression. Therefore, the monoclonal antibody of the present invention is expected to be useful for prevention and diagnosis of infertility and cancer.

The present invention will be further explained with reference to the following non-limiting examples.

Example 1

Preparation of Hybridoma

1. Antigen Preparation

One hundred grams of liver, muscle, and kidney of C3H mouse strain were homogenized in 500 ml of 50 mM triethanolamine buffer (pH8.2) containing 0.1% mercaptoethanol and 1 mM of EDTA. After the homogenate was cetrifuged at 40,000 rpm for 90 minutes, the supernatant was collected. Ammonium sulfate was added to the obtained supernatant to prepare a fraction of 80% ammonium sulfate and then the resulting mixtures were centrifuged at 10,000 rpm for 30 minutes to collect a precipitate. After the precipitate was dissolved in triethanolamine buffer which had the same composition as shown above except that it contained 0.3M KCl, insoluble components were removed by centrifugation at 10,000 rpm for 30 minutes and a supernatant was collected. The supernatant was fractionated by molecular sieve column chromatography Sephacryl S-300. After the glucose phosphate isomerase activity of each fraction was detected and active fractions were combined, the active fraction was dialyzed against PBS to prepare an antigen solution. The concentration of the antigen was adjusted to 1 mg/ml by adding PBS to the antigen solution.

2. Immunization

The obtained antigen solution (1 mg/ml) was mixed with Freund's complete adjuvant in a ratio of 1:1 and an emulsion thereof was prepared by ultrasonic apparatus. ( BALB/c× SJL/J ) F1 (female, 7–8 weeks) was immunized by a priming injection of 0.3 ml of the emulsion intralymphonodically and intradermically and a first booster immunization by injecting 0.3 ml of the emulsion 4 weeks after the priming injection. The blood was sampled from the tail vein of the immunized mouse 1 week after the booster immunization. Antibody production of the immunized mouse was detected by the immunohistochemical method and Western blotting using cultured cells prepared with embryos derived from C3H and BALB/c mouse strains.

The production of anti-mouse antibody specific to mouse strains was detected by the immunohistochemical method using cultured cells of embryos derived from each mouse strain and the specificity of the anti-mouse antibody was examined by Western blotting.

One month after the priming injection, the first booster immunization was carried out and the blood was sampled from the tail of each mouse 1 week after the first booster immunization. After the sampled blood was coagulated at room temperature, it was centrifuged at 3,000 rpm for 20 minutes and the serum was collected. For assay of the antiserum, primary cultured cells prepared with 10-day embryos derived from each mouse strain were immunohistochemically stained and antibody production was detected. Embryos taken from each mouse were washed with PBS, chopped with scalpel or razor and digested with a PBS solution containing 5% trypsin and 0.25% EDTA to obtain separated cells. After the enzyme activity was inactivated by adding 10% fetal calf serum-containing medium, the cells were incubated on sterilized slide glass or cover glass for 24 hours. The incubated cells attached to the glass were fixed by immersion in 95% ethanol fixing solution containing 1% acetic acid at 0° C. for 1 hour and dehydrated with absolute ethanol. The fixed cells were immersed in water and fully washed with PBS. The obtained cells were reacted with PBS containing 5% normal goat serum and 1% bovine serum albumin (BSA) for 30 minutes to block non-specific adsorption. The blocking solution was blotted by filter paper and then each antiserum diluted 1000-fold with a blocking solution was layered on the fixed cells derived from each mouse strain. After the fixed cells were reacted with the antiserum at room temperature for 1 hour, the reacted cells were washed with cold PBS for 15 minutes three times. Subsequently, the obtained cells were reacted with fluorescent anti-mouse antibody (available from Zymed Co.) diluted with the blocking solution to a concentration of 10μg/ml at room temperature for 1 hour and washed in the same way. The reacted cells were encapsuled using 40–50% glycerin-containing PBS as a mount solution and then antigen-antibody complexes were detected with a fluorescent microscope. The immunostaining was carried out in a humid box and the samples were kept moisture. The antiserum containing antibody which is able to combine with the antigen expressed positive granules in the cytoplasm. The mice which produced antiserum showing positive reactivity only with the cells derived from C3H (i.e., they did not express positive granules after the reaction with fixed BALB/c mouse-strain cells) were selected.

The specificity of the antiserum was examined by Western blotting as follows:

Liver and kidney were excised from C3H mouse strain. A buffer such as PBS, TBS or the like was added to the above organs in an amount of 10 ml per 1 g of the organs and subsequently the organs were homogenized by ultrasonic mastax. The obtained homogenate was cetrifuged at 40,000 rpm and soluble components in the supernatant were collected. After the proteins contained in the thus-obtained solution were denatured by heating in the presence of β-mercaptoethanol, the protein components were separated by SDS-polyacrylamide gel electrophoresis according to a conventional method. The electrophoresis was carried out using minigel which was 10 cm long, 10 cm wide and 1 mm thick and which comprised 4% stacking gel and 10% homogenous polyacylamide slab gel for separation.

After the electrophoresis, the gel was brought into close contact with nitrocellulose membrane and then the proteins separated in the gel were transferred from the gel to the membrane in Tris-glycine solution (0.025M–0.195M) containing 10% of methanol but not containing SDS, at 4° C. for 10 hours at a voltage of 50 V. The membrane was immersed into TBS (blocking solution) containing 5% normal goat serum and 1% BSA at room temperature for 30 minutes to block non-specific adsorped portions of the proteins. Subsequently, the serum which showed positive reactivity in the immunohistochemicai method was reacted with the solution diluted 300-fold with the blocking solution at room temperature for 2 hours. After being washed with cold TBS for 15 minutes three times, the mixtures were reacted with goat anti-mouse IgG antibodies diluted with the blocking solution to a concentration of 10 μ g/ml for 2 hours at room temperature and then washed in the same way as set out above. The reaction mixtures were reacted with mouse PAP solution diluted with the blocking solution to a concentration of 40μ g/ml for 2 hours and fully washed with cold TBS. The reaction mixtures were immersed into a color producing reagent which comprised 20 mg of diaminobendizine, 15 mg of cobalt chloride and 50 μl of hydrogen peroxide in 50 ml of TBS (pH 7.6). The antiserum which reacted with a protein having a molecular weight of 66,000 and a protein having a molecular weight of 68,000 was selected by detecting positive bands.

The emulsion (0.3 ml) was intralymphonodically and intradermically injected up to 5 times every 2 week to individuals which showed low antibody titer, that is, antibody titer of 10–20 time-dilution represented by degree of dilution of the antiserum used for the immunohistochemical assay, and to individuals which produced no antibody. The final immunization was carried out by injecting 0.3 ml of the emulsion to a mouse producing an antibody which specifically recognized cells derived from C3H strain but did not recognize cells derived from BALB/c strain.

3. Preparation of Hybridoma

The spleen cells were removed from the immunized mouse from 3 to 4 days after the final immunization and washed with serum free RPMI1640 medium. Mouse myeloma NS-1 cells were washed in the same way. After the spleen cells were mixed with the myeloma cells in a ratio of 5:1 and the mixtures were centrifuged, 1 ml of RPMI1640 solution containing 50% PEG4000 (available from Seakem) was gradually added to the cell pellet and cell fusion was carried out at 37° C. for 3 minutes. Additional RPMI1640 solution was added to the resulting cell mixtures and the cell mixtures were diluted with PEG solution to 10 ml of total volume. After further centrifugation, the cell mass was suspended in RPMI1640 medium containing 20% fetal calf serum and HAT in a NS-1 density of $1 \times 10^5$ cells/0.1 ml and 0.1 ml of the cell suspension was placed in each well of a 96-well microplate in which $5 \times 10^3$ cells/well of macrophages as feeder cells were previously cultured. The macrophages as feeder cells were obtained by a method which comprises injecting i.p.0.5 ml of a mineral oil such as pristane (2,6,10,14-tetramethyl pentadecane) to BALB/c mouse, washing the abdominal cavity with a medium 1 week thereafter to collect macrophages. One-half of the culture medium was replaced with fresh HAT medium every 3 or 4 days. About seven days after the cell fusion, hybridoma cells were growing in several wells. About 10–14 days after the cell fusion, one-half of the culture medium was replaced every three days with fresh HT medium, which is a medium that removes aminopterin from HAT medium. About 10 days after starting the replacement with HT medium, the cell culture was continued in conventional RPMI1640 medium containing 20% fetal calf serum.

4. Detection of Antibody-Producing Cells

The antibody-producing cells in the supernatant of the well in which hybridoma cells grew were detected by the immunohistochemical method using embryo cultured cells derived from C3H and BALB/c mouse strains. The specificity thereof was examined by Western blotting.

(1) Immunohistochemical Method

Ten-day embryos derived from each strain (C3H and BALB/c) were taken from the uterus of the mother, washed with PBS and then chopped with a scalpel and razor. The chopped tissues were digested with a solution comprising 0.25% trypsin and 0.25% EDTA to obtain separated cells. The enzyme activities of trypsin were inactivated by adding a medium containing 10% fetal calf serum. After the cells were centrifuged, the cell mass was suspended in a medium containing 10% fetal calf serum and then the suspended cells were incubated on sterilized slide glass or cover glass for 24–48 hours. The incubated cells attached to the glass were fixed by being immersed in a fixing solution comprising 95% ethanol and 1% acetic acid for about 1 hour, dehydrated with absolute ethanol, dried and then preserved in a freezer at −20° C. The fixed cells were immersed in PBS to return them to the wet condition and then reacted with PBS containing 5% normal goat serum and 1% BSA for 20–30 minutes to block non-specific adsorption. The blocking solution was blotted by filter paper and then about 20–50 μl of the culture supernatant of hybridomas were layered on the above fixed cells derived from each strain and reacted with the fixed cells for about 1 hour at room temperature. After being fully washed with PBS, the reacted cells were reacted with fluorescent anti-mouse antibody (5 μl/ml) for about 40 minutes to 1 hour at room temperature. The resulting cells were encapsuled with PBS containing 40–50 % glycerin and then antigen-antibody complexes were detected with a fluorescent microscope. Fluorescent granules were detected in the cytoplasm of a cell to which the culture supernatant containing an antibody which is able to react with the antigen was added (positive reactivity).

(2) Antibody Preparation

The culture supernatant of the hybridoma was selected which was reactive with the cells derived from C3H strain but was not reactive with fixed BALB/c mouse-strain cells. Cloning of the hydridoma was carried out by limiting dilution. After the presence of a single clone was affirmed by microscope, the culture supernatant of the hybridoma was subjected to the treatment of the above immunohistochemical method to detect and obtain a positively reactive hybridoma. This cloning was carried out three times to obtain hybridoma cell lines of 17-6 and 18-15, each of which is derived from a single clone. The culture supernatants of these hybridoma cells were concentrated with 45% ammonium sulfate fraction and then dialysed against PBS to obtain antibody solutions.

(3) Western Blotting

The soluble components in the liver extract derived from C3H and BALB/c mouse strains were subjected to SDS-polyacrylamide gel electrophoresis according to a conventional method. After the electrophoresis, the gel was brought into close contact with a nitrocellulose membrane (10×10 cm square) and then the proteins separated in the gel were electrically transferred and adsorbed to the nitrocellulose membrane. The nitrocellulose membrane was treated with TBS (50 mM Tris-HCl buffered saline solution, pH7.6) for 20 minutes at room temperature and subsequently reacted for 16 hours with 5 ml of the antibody solution obtained according to the procedures described in (2) in which the concentration of the antibody was adjusted to a final concentration of 5–10μg/ml using a blocking solution. After being fully washed with TBS, the mixtures were reacted for 1 hour with 5 ml of rabbit anti-mouse antibodies diluted with the blocking solution to a concentration of 10μg/ml and then fully washed with TBS. The reaction mixtures were reacted for 1 hour with 5 ml of mouse PAP (peroxidase- anti-peroxidase) solution diluted with the blocking solution to 40 μ g/ml and washed with TBS. The color producing reaction of the resulting mixtures was carried out using diaminobendizine-cobalt chloride-hydrogen peroxide reaction solution which comprised 20 mg of diaminobendizine, 15 mg of cobalt chloride and 50 μl of hydrogen peroxide in 50 ml of TBS. It was found that the monoclonal antibody produced by the 17-6 cell line as well as that produced by the 18-15 cell line recognized protein bands of 66,000 and 68,000 dalton separated from the extract of C3H mouse liver but did not recognize either the other proteins separated therefrom or proteins derived from other than C3H strain. The hybridoma cell lines, 17-6 and 18-15, were deposited with the Fermentation Research Institute, Agency of Industrial Science and Technology, 1-3, Higashi 1-chome, Tsukuba city, Ibaraki, 305 Japan and have accession numbers FERM BP-3763 and BP-3764, respectively.

Example 2

Production of Monoclonal Antibody

Hybridoma 17-6 and 18-15 cell lines were cultured, respectively in RPMI1640 medium containing 20% fetal calf serum scaling up the production of the antibodies by culturing the hybridoma cells in a 96-well plate, then in a 25 cm$^2$ flask and finally in a 75 cm$^2$ flask, and the supernatants were recovered. Further, each cell line of the hybridomas was i.p. injected to nude mice to form an ascites tumor. Ten days after the injection, the ascites was recovered. The antibody contained in the ascites was purified by the affinity column method using protein G. The specificity of the obtained antibody was examined by the same monoclonal antibody immunohistochemical method and Western blotting as in Example 1.

Reference Example 1

Characterization of Monoclonal Antibody

1. Determination of Subclass of Monoclonal Antibody

Each monoclonal antibody was coated on a 96-well soft microtiter plate and blocked with PBS containing 1% BSA. Then the reactivity of the monoclonal antibodies with anti-IgA antibody, anti-IgG1 antibody, anti-IgG2a antibody, anti-IgG2b antibody, anti-IgG3 antibody and anti-IgM antibody was tested using a MONOABID EIA KIT (available from ZYMED Co.) to determine the subclass of the obtained monoclonal antibodies. The type of the monoclonal antibodies was determined by the reactivity of L chain with anti-λ antibody and anti-κ antibody. It was found that both the monoclonal antibody produced-by 17-6 cell line and that produced by the 18-15 cell line were of IgG1/ κ subclass. The monoclonal antibody produced by the 17-6 cell line and that produced by the 18-i5 cell line will be hereinafter referred to as monoclonal antibody A and monoclonal antibody B, respectively.

2. Investigation of Mouse Strains Using Monoclonal Antibody

The strain specificity of monoclonal antibody A to the cells derived from a variety of mouse strains was examined by Western blotting. As a result, mouse strains of DBA/1J, CE/J, SM/J, PL/J, SWM/Ms, IQI, RIII S/J and RFM/MsNrs and C3H congenic strains of C3H NB/sn, C3H SW/snJ, C3HJKrsn, C3H/He, C3H OL/N, C3H He-Ha Pgk-1a, C3H He sn-Ttf/+tf, C3H-Ttf/to+, C3H-Ttf/tw18tf, C3H-eB/Fej-nr and C3H OH/J expressed antigens to monoclonal antibody A. On the other hand, mouse strains of A/wySnJ, B10/SnJ, CBA/J, AKR/J, CBA/CaHN, P/J, C57BR/cdJ, PT, C58/J, C57BL/6J, C57L/J, SWR/J, 129/J, SJL/J, GRS/A, BALB/cUcsd, CBA/StMs, HRS/J, 1/LnJ, A2G/OLA//HSD, BALB/cByJ, BALB/cJ, C57BL/6ByJ, MA/MyJ, WB/ReJ-W, BALB/cAnN, DBA/2J, NZB/B1NJ and DM/Shi did not express antigens to monoclonal antibody A.

The strain specificity of monoclonal antibody B to the cells derived from a variety of mouse strains was examined by the same method. The same results were obtained.

3. Antigen

Antigens present in the above positive mouse strains were analyzed by Western blotting. It was found that both monoclonal antibody A and monoclonal antibody B recognized antigen having a molecular weight of 68,000 and that having a molecular weight of 66,000. Further, components contained in the cytoplasm of the above positive mouse strains were centrifuged and then each fraction was examined by Western blotting. The antigens were found to be located in the mitochondria.

4. Location of Antigen

The cells of the positive mouse strains were treated by immune double stain using rabbit antiserum to mitochondrial complex II located in the mitochondria of rat and monoclonal antibody A and the stained cells were observed by microscope. The portions recognized by monoclonal antibody A completely overlapped those recognized by the rabbit antiserum. This result showed that monoclonal antibody A recognized an antigen located in the mitochondria.

The above procedures were repeated except that monoclonal antibody B was used instead of monoclonal antibody A. The same results were obtained.

5. Genetic Analysis of Antigen

For assay of the mouse antigens recognized by monoclonal antibody A, a back cross experiment between C3H inbred strain mice and BALB/c inbred strain mice was carried out. The results are shown in Table 1.

Table 1

Genetic Analysis of Strain Specific Antibody by Back Cross

| Male | Female | Number of Litter | Number of Progeny | Result (Expectation) + | − | $\chi^2$ value | accept/reject |
|---|---|---|---|---|---|---|---|
| BALB/c | BAC3 | 5 | 53 | 22 | 31(1:1) | 1.53 | accept |
| BALB/c | C3BA | 6 | 63 | 37 | 26(1:1) | 1.92 | accept |
| BAC3 | BALB/c | 7 | 53 | 22 | 31(1:1) | 1.53 | accept |
| C3BA | BALB/c | 7 | 43 | 17 | 26(1:1) | 1.88 | accept |
| | | | (F1 × F1) | | | | |
| BAC3 | BAC3 | 7 | 58 | 42 | 16(3:1) | 0.21 | accept |
| C3BA | C3BA | 4 | 27 | 20 | 7(3:1) | 0.0124 | accept |

Note:
$\chi^2$ value(accept/reject), df = 1, α = 0.05, rejected if $\chi^2$ > 3.84
BAC3: (BALB/c♀ × C3H/HeN♂)F1, C3BA: (C3H/HeN♀ × BALB/c♂)F1

The results showed that a gene encoding for the antigen which was recognized by monoclonal antibody A was present in genomic DNA, controlled according to Mendel's law and derived from a single gene.

Example 3

Immunohistochemical Analysis of Chimerism of Chimera Mouse Tissues

A chimera mouse which was developed by aggregating 8-cell stage embryos derived from two inbred strain mice is constituted with at least two kinds of genetically independent cell populations. The method for analyzing at the tissue level the origin of the cells which constitute chimeric tissues is an effective tool for investigating of cell renewal systems and cell-lineage. The antigen recognized by the monoclonal antibody maintains antigenicity in a general cultured cell after being treated with a fixing solution comprising 95% ethanol and 1% acetic acid. However, tissues are not stably fixed with such mild fixing solutions and the structure of the tissues is not stable. Therefore, the tissues were fixed by perfusion fixation from the heart after the fixing solution was cooled to 0° C. Alternatively, the tissues were fixed by a method which comprises exposing sliced tissues to microwave radiation by a microwave processing oven (available from Biolad Co.) in 0.1M sodium phosphate buffer at 60% power at 40° C. for 20 minutes; fixing the tissues with a fixing solution comprising 95% ethanol and 1% acetic acid at 0° C. for 5 hours; dehydrating the fixed tissues with absolute ethanol; and embedding the resulting tissues with polyester wax to prepare slices of the tissues having a thickness of 4 μm. The tissues fixed by these fixing methods maintained both the tissue structure and the antigenicity. The sliced tissues were subjected to a dewaxing treatment, washed with PBS and treated with a solution comprising 0.6% hydrogen peroxide and 0.2% NaN$_3$ for 1 hour to inactivate endogenous peroxidase activity. After being fully washed with 20 mM Tris-HCl physiological saline (pH 7.6,TBS), the tissues were reacted with Avidin-Biotin Blocking Kit (available from Vector Co.) solution diluted two-fold with 0.5% fish gelatin/TBS for 20 minutes to block endogenous biotin and non-specific adsorption. The thus-treated tissues were reacted for 1 day at room temperature with biotinylated monoclonal antibody A as a primary antibody diluted with 0.5% fish gelatin solution in TBS to a concentraion of 10 μg/ml. The biotinylated monoclonal antibody was prepared as follows:

The antibody solution was dialysed against 0.1M NaHCO$_3$ and after the dialysis, the dialysed antibody was diluted with 0.1M NaHCO$_3$ to a concentraion of 1 mg/ml. NHS-LC-biotin (available from Pierce Co.) was dissolved in DMSO (available from Sigma Co.) to a concentration of 1 mg/ml. The obtained antibody solution was mixed with the above biotin solution in a ratio of 60 μl of the biotin solution to 1 ml of the antibody solution and the mixtures were reacted at room temperature for 4 hours. After the reaction, the reaction mixtures were dialysed against PBS containing 0.1% NaN$_3$.

After being washed with PBS, the sliced tissues reacted with the biotinated monoclonal antibody A were reacted for about 20 minutes with avidin-peroxidase (available from ZYMED Co.) as a secondary antibody diluted 100-fold with 0.5% fish gelatin solution in TBS (pH 8.0). The reacted tissues were washed with TBS and then 150 ml of an aqueous solution comprising 40 mg of diaminobendizine (DAB) and 40 μl of hydrogen peroxide were added thereto. Tris-HCl buffer (50 mM) was added to the solution to adjust the pH to 7.6 and then a color producing reaction was carried out for 1–2 minutes. After being washed with distilled water, the resulting sliced tissues were reacted with 0.1% gold chloride solution for 5 minutes, washed with distilled water, immersed in 2.5% sodium sulfide solution (pH7.4) for 5 minutes and washed with distilled water. The obtained tissues were immersed in a silver stain (composition in 150 ml of the silver stain: 3.11 g of Na$_2$CO$_3$, 0.15 g of NH$_4$NO$_3$, 0.15 g of AgNO$_3$, 0.75 g of silico tungsten acid and 0.274 ml of 35% formalin in H$_2$O) for 1 minute and the silver stain was stirred. After color development, the sliced tissues were rapidly transferred to 1% acetic acid solution to stop the reaction with a silver. The stained tissues were fixed with 1% aqueous solution of sodium thiosulfate and washed with distilled water. The resulting tissues were subjected to hematoxylin-eosin staining according to a conventional method and then covered with a cover glass. Observation by microscope revealed that the chimeric tissues were constituted of positive cells which were stained with monoclonal antibody A and negative cells which were not strained therewith. The chimerism of viviparous early embryo was effectively analyzed using microwave fixing. In the tissues of an adult chimera mouse, the anagenetic system was classified on the basis of the chimerism as follows:

1: tissues characterized in that the anatomical tissue unit is constituted of cells derived from only one strain (for example, small intestinal crypt).

2: tissues characterized in that the anatomical tissue unit is constituted of cells derived from both strains (for example, exocrine gland acinus).

3: tissues characterized in that the anatomical tissue unit is unclear and the growing unit is observed by chimerism (for example, skin).

4: tissues characterized in that the anatomical tissue unit is not present and the growing unit is not observed by chimerism (for example, connective tissue and muscular tissue).

The above procedures were repeated except that monoclonal antibody B was used instead of monoclonal antibody A. The same results were obtained.

What is claimed is:

1. A method for identifying the origin of a cell from a chimeric mouse, derived from strain DBA/1, CE/J, SM/J, IQI, PL/J, SWM/Ms, RIII/J or RFM/MsNrs comprising:
    a) reacting said cell with a monoclonal antibody of IgG1/κ subclass, characterized in that said monoclonal antibody recognizes antigens specifically present in mouse inbred strains DBA/1, CE/J, SM/J, IQI, PL/J, SWM/Ms, RIIIS/J, and RFM/MsNrs, wherein one of said antigens has a molecular weight of 66,000 and another of said antigens has a molecular weight of 68,000 and said antigens are present in the mitochondria of strain C3H, wherein said chimeric mouse is also derived from a strain which does not contain said antigens, and
    b) detecting said antigens in said cell with said monoclonal antibody; thereby indicating said cell is derived from DBA/1, CE/J, SM/J, IQI, PL/J, SWM/Ms, RIIIS/J, or RFM/MsNrs.

2. The method according to claim 1, which further comprises fixing said cell, and detecting the reaction immunohistochemically.

3. The method of claim 1 wherein said antibody is produced by a hybridoma cell line designated FERM BP-3763.

4. The method of claim 1 wherein said antibody is produced by a hybridoma cell line designated FERM BP-3764.

* * * * *